(12) United States Patent
Perez-Cruet et al.

(10) Patent No.: US 7,803,159 B2
(45) Date of Patent: Sep. 28, 2010

(54) DISC SPACE PREPARATION DEVICE FOR SPINAL SURGERY

(75) Inventors: Miquelangelo J. Perez-Cruet, Bloomfield, MI (US); John R. Pepper, Cheshire, CT (US); John A. Miller, Bloomfield Village, MI (US)

(73) Assignee: MI4Spine, LLC, Bloomfield Hills, MI (US)

( * ) Notice: Subject to any disclaimer, the term of this patent is extended or adjusted under 35 U.S.C. 154(b) by 973 days.

(21) Appl. No.: 11/605,641

(22) Filed: Nov. 29, 2006

(65) Prior Publication Data

US 2008/0125783 A1  May 29, 2008

(51) Int. Cl.
*A61B 17/00* (2006.01)
(52) U.S. Cl. .......................................... 606/80; 606/79
(58) Field of Classification Search ............. 606/79–81, 606/168, 180; 37/250, 420; 30/205, 240, 30/278; 73/864.43; 408/214
See application file for complete search history.

(56) References Cited

U.S. PATENT DOCUMENTS

| 4,649,919 | A | * | 3/1987 | Thimsen et al. ............... 606/80 |
| 5,084,052 | A | | 1/1992 | Jacobs |
| 5,925,056 | A | * | 7/1999 | Thomas et al. ............... 606/180 |
| 6,066,153 | A | * | 5/2000 | Lev ............................. 606/180 |
| 6,358,252 | B1 | * | 3/2002 | Shapira ....................... 606/80 |
| 6,783,533 | B2 | | 8/2004 | Green et al. |
| 2004/0193170 | A1 | | 9/2004 | Kemppainen et al. |
| 2005/0154460 | A1 | | 7/2005 | Yundt |
| 2006/0149280 | A1 | | 7/2006 | Harvie et al. |

* cited by examiner

*Primary Examiner*—Thomas C Barrett
*Assistant Examiner*—Andrew Yang
(74) *Attorney, Agent, or Firm*—John A. Miller; Miller IP Group, PLC

(57) ABSTRACT

A disc space preparation device that has particular application for removing disc material during spinal fusion surgery. The disc preparation device includes a body portion that houses a motor having a shaft attached thereto that is rotated by the motor. The shaft extends through a chamber in a neck portion of the device and into an open head portion of the device at the end of the neck portion opposite to the housing. The head portion rotates relative to the neck portion. The head portion includes a series of blades that are used to cut-away the disc material. The shaft includes an auger that draws the cut material through the neck portion. A suction port is coupled to the chamber in the neck portion to remove the disc material therefrom.

20 Claims, 3 Drawing Sheets

DISC SPACE PREPARATION DEVICE FOR SPINAL SURGERY

BACKGROUND OF THE INVENTION

1. Field of the Invention

This invention relates generally to a disc space preparation device for spinal surgery and, more particularly, to a disc space preparation device for spinal surgery that includes an outer cutting blade and an auger for removing cut disc material from the surgical area.

2. Discussion of the Related Art

The human spine includes a series of vertebrae interconnected by connective tissue referred to as disks that act as a cushion between the vertebrae. The disks allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal disks, abnormal spinal curvature and a weak or unstable spine.

In an attempt to preserve normal anatomical structures during spine surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filled with the graft material. This procedure is referred to as interbody fusion since it is between adjacent vertebrae. The cage includes holes that allow the vertebrae and the graft material to grow together to provide the fusion. The cage supports the weight of adjacent vertebrae while the fusion is occurring through the cage. Alternatively, the bone graft material can be placed directly over or lateral to the spine, referred to as postero-lateral fusion. Typically the bone graft material is autogenous bone material taken from the patient, or allograft bone material harvested from cadavers. Synthetic bone materials can also be used as the graft material. Generally, the patient's own bone material offers the best fusion material and is the current "gold standard".

Spinal instrumentation is then performed to immobilize the vertebral segments where the bone is placed. Similar to the function of wearing a cast or brace after breaking a long bone, spinal instrumentation allows for immobilization, which promotes bone fusion. One of the most common forms of spinal instrumentation is a pedicle screw and rod construct. The rods, which span adjacent vertebrae, are mounted to the vertebra using pedicle screws that are threaded through the pedicles of each vertebra and into the vertebral body. Accurate placement of the pedicle screws relative to the vertebral pedicle is very important to prevent injury to nerves or spinal cord. Typically, fluoroscopy is used to ensure that the pedicle screws are properly oriented relative to the pedicle.

During spinal fusion surgical procedures, it is necessary to completely remove the disc and clean out the disc space between the vertebrae being fused. Particularly, it is necessary to remove as much of the disc material as possible between the vertebrae so that the graft material that will be provided between the vertebrae for the fusion provides a good bone-to-bone adhesion. Any remaining disc material that is not removed reduces the chance that the graft material will provide the bone graft adhesion necessary for a satisfactory fusion process.

Currently, various surgical devices are used in the art to remove the disc material for both minimally invasive and open spinal fusion procedures. For minimally invasive spinal surgery, a cutting device, such as a pituitary rongeur, is used to remove the disc material. The pituitary rongeur is a mechanical device including a "cup end" that cuts and scoops out the disc material to remove it in a mechanical operation. Manipulating the cup end of the pituitary rongeur is relatively cumbersome in that it is limited in its ability to clear the disc space around corners and other "guarded" areas proximate to the vertebrae. Further, because the pituitary rongeur is a mechanical device, it is limited in its ability to protect sensitive parts of the vertebrae, such as spinal nerves running through the disc space.

SUMMARY OF THE INVENTION

In accordance with the teachings of the present invention, a disc space preparation device is disclosed that has particular application for removing disc material during spinal fusion surgery. The disc space preparation device includes a body portion that houses a motor having a shaft attached thereto that is rotated by the motor. The shaft extends through a chamber in a neck portion of the device, and into an open head portion of the device at the end of the neck portion opposite to the housing. The head portion includes a series of blades that are used to cut-away the disc material. The shaft includes an auger that draws the cut material through the neck portion. A suction port is coupled to the chamber in the neck portion to remove the disc material that is drawn away by the auger.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a disc space preparation device is merely exemplary in nature, and is in no way intended to limit the invention or its applications or uses. For example, the disc space preparation device of the invention has particular application for removing disc material during spinal fusion between adjacent vertebrae being fused. However, as will be appreciated by those skilled in the art, the disc space preparation device of the invention may have application for other surgical and non-surgical operations.

Figure 1:
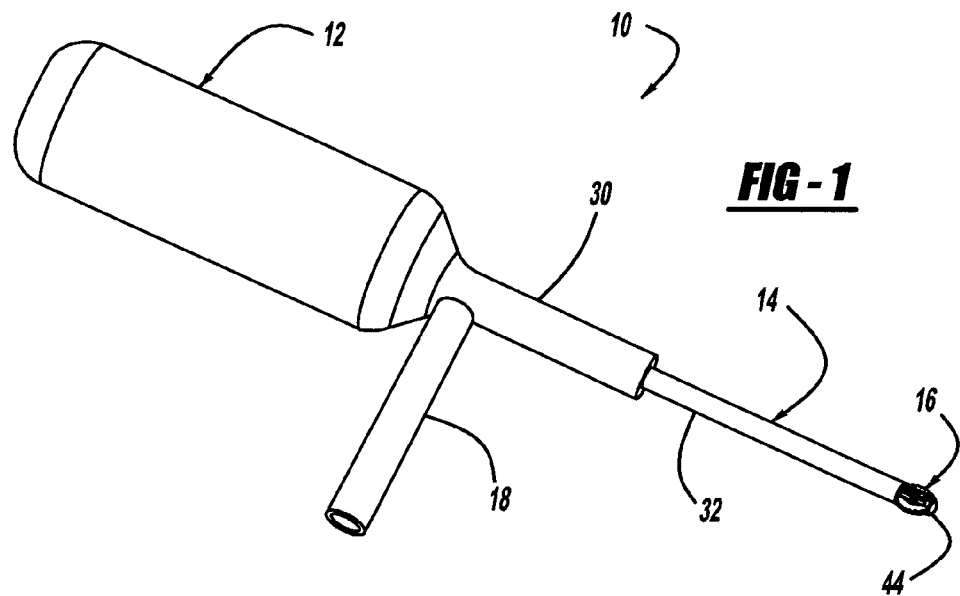
FIG. 1 is a perspective view of a disc space preparation device for spinal fusion surgery, according to an embodiment of the present invention.
Figure 2:
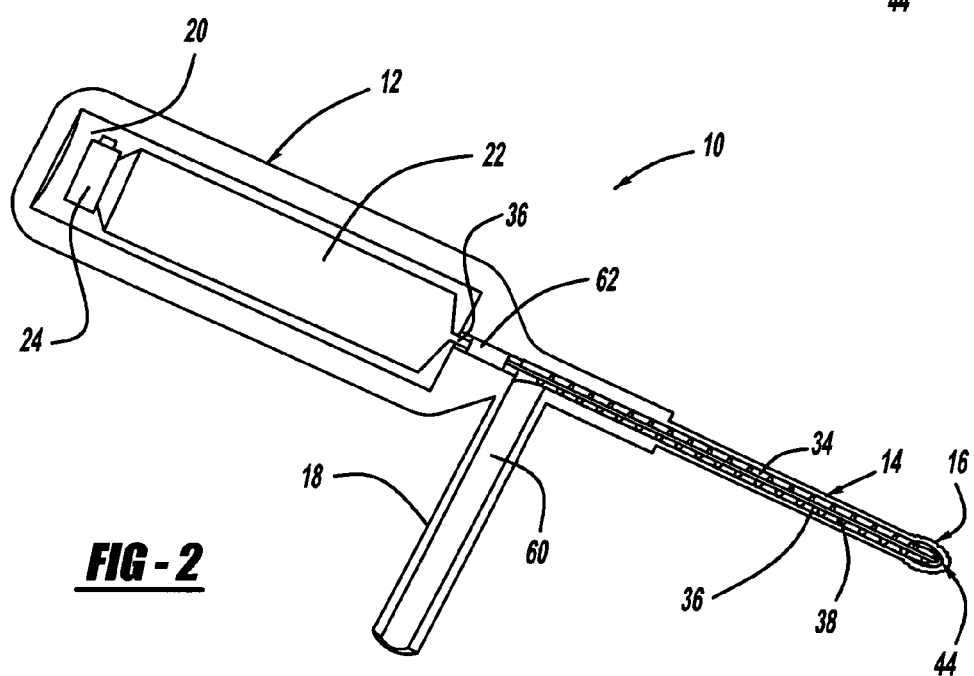
FIG. 2 is a broken-away perspective view of the disc space preparation device shown in FIG. 1.

FIG. 1 is a perspective view and FIG. 2 is a cut-away, perspective view of a disc space preparation device 10, according to an embodiment of the present invention. The disc space preparation device 10 includes a body portion 12, an elongated neck portion 14 attached to the body portion 12, an open cutting head portion 16 attached to the neck portion 14 opposite to the body portion 12, and a suction port 18. The body portion 12 includes an internal chamber 20 in which is mounted an electric motor 22. The electric motor 22 can be a DC motor powered by batteries 24 or an AC motor powered by an electrical power cord (not shown). Alternately, the motor 22 can be eliminated and the device 10 can be pneumatic or vacuum driven.

In this non-limiting embodiment, the elongated neck portion 14 has a step configuration including a wider diameter portion 30 and a narrow diameter portion 32, where the wider portion 30 provides increased stiffness. The neck portion 14 further includes a neck chamber 34 that is in fluid communication with the open cutting head portion 16. A shaft 36 is coupled to the motor 22, and extends through the neck chamber 34. The shaft 36 includes a screw or auger 38 for reasons that will become apparent from the discussion below. When the motor 22 is turned on, the shaft 36 and the auger 38 rotate. In one non-limiting embodiment, the auger 38 has a pitch-to-diameter ratio of about 1:1. Further, the neck portion 14 can be made of a suitable low friction material, such as stainless steel, to support the rotation of the auger 38.

Figure 3:
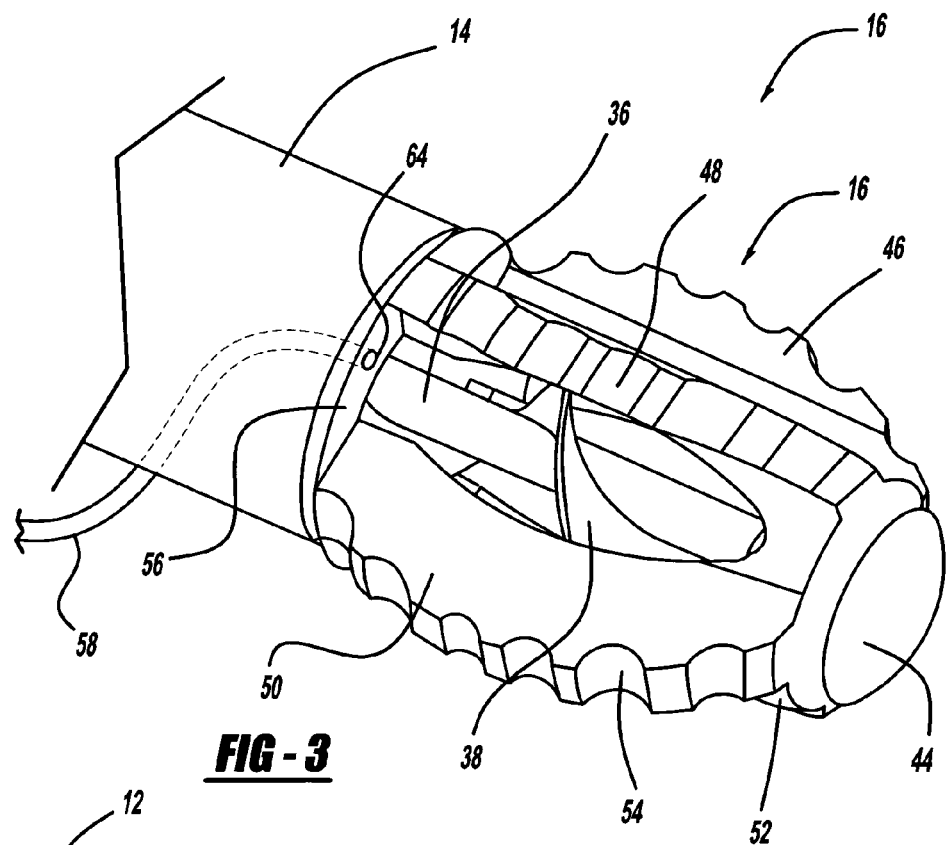
FIG. 3 is a perspective view of a head portion of the disc space preparation device shown in FIG. 1.

FIG. 3 is a perspective view of the head portion 16. The head portion 16 includes an end cap 44 in which an end of the shaft 36 can be rotatably mounted by bearings or the like. The end portion 16 also includes four symmetrically disposed cutting blades 46, 48, 50 and 52 each having a serrated cutting edge 54, although the cutting edge does not need to be serrated for other embodiments. The head portion 16 is open to the chamber 34 between the cutting blades 46-52, as shown. The head portion 16 is mounted to the neck portion 14 so that it rotates relative to thereto in any suitable manner. The cutting blades 46-52 can be made of any suitable material, such as stainless steel. In this embodiment, the cutting blades 46-52 have a general arced configuration. However, this is by way of a non-limiting embodiment, in that any cutting blade configuration suitable for the purposes described herein can be employed.

During the disc preparation part of spinal fusion surgery, the surgeon will grasp the body portion 12, and position the cutting blades 46-52 within the disc space through an incision in the patient. The surgeon then causes the end portion 16 to rotate to rotate the cutting blades 46-52 to cut away the disc material. The cutting blades 46-52 shield the auger 38 so that it does not contact the tissue. The neck portion 14 and the cutting head portion 16 have a size that is suitable for minimally invasive spinal surgical procedures. In one non-limiting embodiment, the neck portion 14 is about 9 inches long and the narrow portion 32 has a diameter of about 8 mm. As the cutting blades 46-52 cut away the disc material, the disc material will fall into the open spaces between the cutting blades 46-52. As the shaft 36 rotates, the auger 38 will draw away the cut disc material through the chamber 34 towards the motor 22. The head portion 16 and the auger 38 can be rotated in opposite directions for maximum efficiency. The stepped configuration of the neck portion 14 allows for more material to be collected in the neck chamber 34 opposite to the head portion 16.

In this non-limiting embodiment, the diameter of the auger 38 is slightly less than the diameter of the chamber 34 so that the auger nearly completely fills the chamber 34 and is able to easily rotate therein. An annular shredding member 56 is provided between the head portion 16 and the neck portion 14. The shredding member 56 has a relatively sharp cutting edge that acts to shred larger pieces of material that have been cut and are being drawn away by the auger 38 so that they can easily travel through the chamber 34. An edge of the auger 38 can also be equipped with a scraper (not shown) to prevent clogging within the neck chamber 34. Further, the auger 38 can include teeth (not shown) to reduce the size of the material being cut away. Also, an irrigation line 58 can be provided that emits water or some other lubricant into the head portion 16 through an orifice 64 so that the water is drawn up the neck portion 14 by the auger 38 and acts to lubricate the chamber 34 and help draw the material out of the neck portion 14.

The suction port 18 includes a channel 60 that is in fluid communication with the chamber 34. A suction line (not shown) is coupled to the suction port 18 and sucks the cut away material out of the chamber 34 using a vacuum pump (not shown). A seal 62 is provided around the shaft 36 between the motor chamber 20 and the chamber 34 to prevent the material that is cut away from entering the body chamber 20. In this manner, the device 10 can be used to accurately and quickly remove the disc material between the vertebrae being fused during the surgical procedure, especially around the edges and contours of the vertebra.

Figure 4:
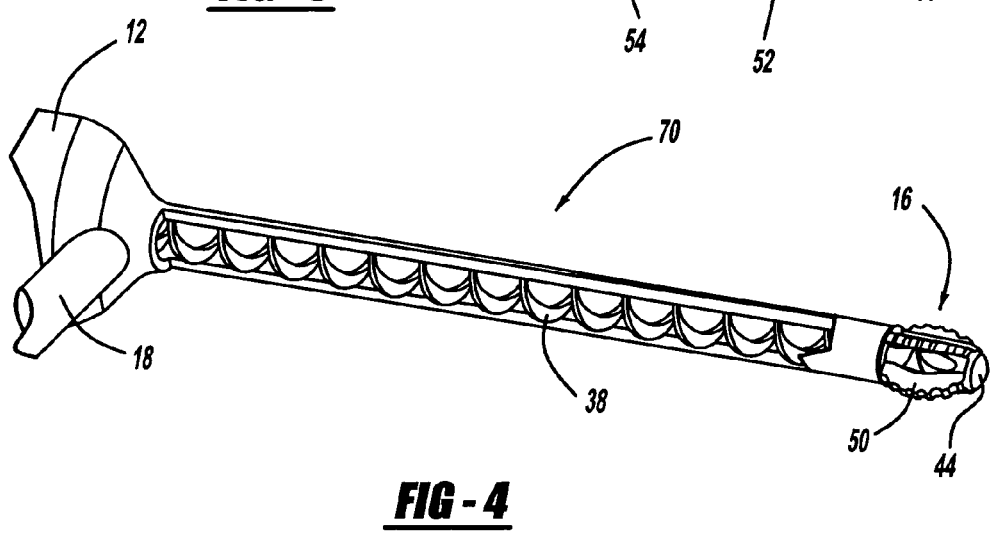
FIG. 4 is a broken-away perspective view of a disc space preparation device including an auger without a center shaft, according to another embodiment of the present invention.

FIG. 4 is a cut-away perspective view of a disc space preparation device 70, according to another embodiment of the present invention, where like components to the disc space preparation device 10 are identified by the same reference numeral. In this embodiment, the shaft 36 has been eliminated where the auger 38 alone rotates within the chamber 34. This configuration will reduce the cost and weight of the device 70.

Figure 5:
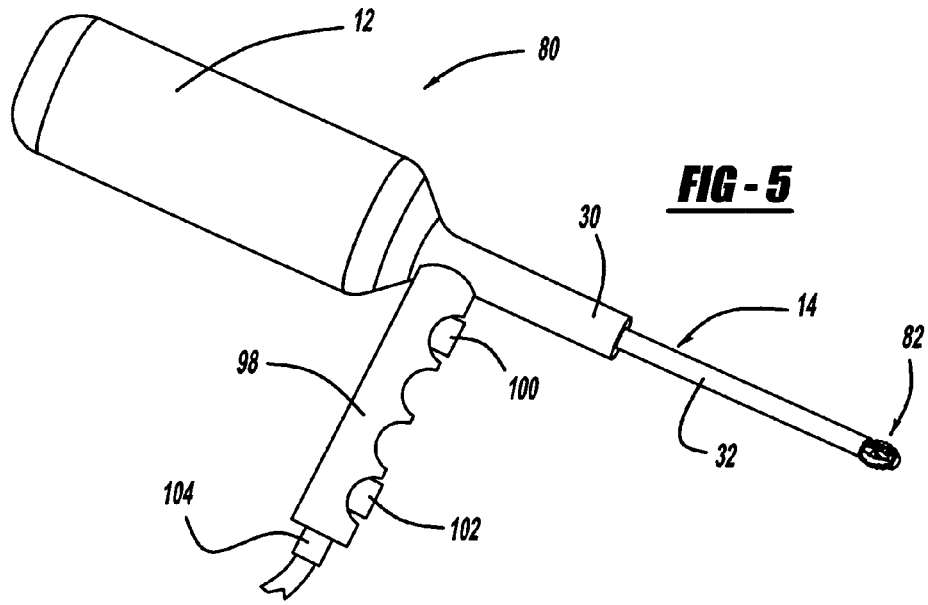
FIG. 5 is a perspective view of a disc space preparation device employing a pistol grip and a rotating cutting head portion, according to another embodiment of the present invention.
Figure 6:
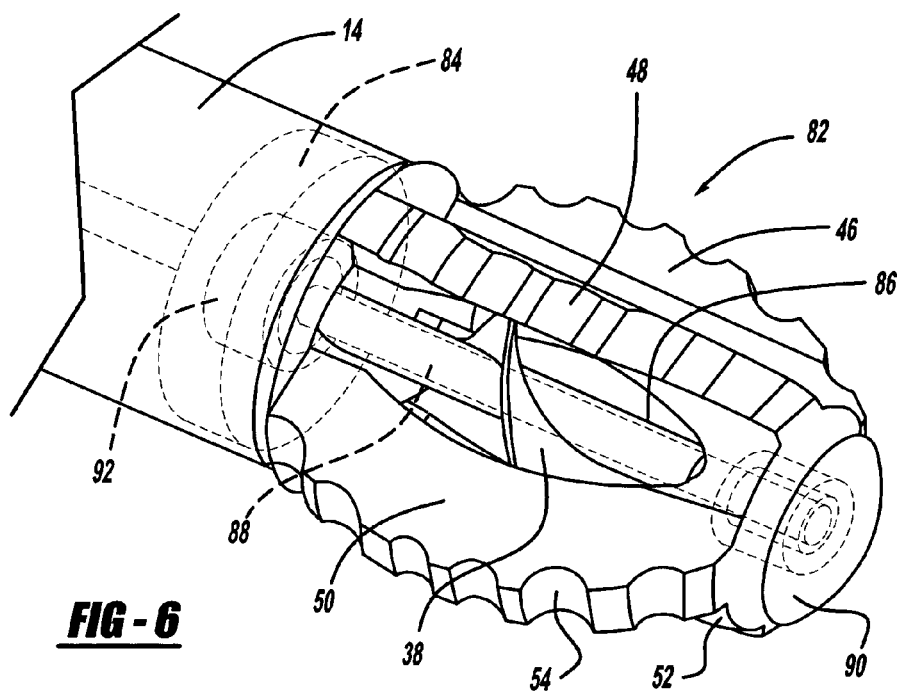
FIG. 6 is a perspective view of the head portion of the device shown in FIG. 5.

FIG. 5 is a perspective view of a disc space preparation device 80, according to another embodiment of the present invention, where like elements to the disc space preparation device 10 are identified by the same reference numeral. The disc space preparation device 80 includes a head portion 82 that is rotatable relative to the neck portion 14 on bearings 84 in a manner that would be well understood to those skilled in the art. A close-up view of the head portion 82 is shown in FIG. 6. The device 80 includes an outer shaft 86 and an inner shaft 88 where the shafts 86 and 88 are concentric. The shaft 86 includes an internal bore, where the shaft 88 is easily rotatable therein. The auger 38 is attached to the outer shaft 86. The inner shaft 88 is rigidly coupled to an end cap 90 of the head portion 82 so that when the inner shaft 88 rotates, the head portion 82 rotates on the bearings 84. The outer shaft 86 rotates within the chamber 34 in the same direction or an opposite direction to the inner shaft 88. The rotating head portion 82 causes the blades 46-52 to cut the disc material, and the rotating auger 38 draws the cut disc material away as discussed above.

The shafts 86 and 88 are coupled to a gear system 92 that causes the shafts 86 and 88 to rotate in the same or opposite directions. The gear system 92 can be any suitable gear system for the purposes described herein, such as a planetary gear system.

The device 80 also includes a pistol grip 98 rigidly coupled to the neck portion 14 that allows the surgeon to easily hold on to the device 80. The pistol grip 98 includes an on/off button 100 that can be pressed to turn the device 80 on and be released to turn the device 80 off. A second button 102 can be provided that allows the surgeon to stop the inner shaft 86 from rotating and only allow the outer shaft 86 to rotate for intricate manual cutting where the rotating head portion 82 may be to risky for cutting near a nerve. One skilled in the art would readily understand how to configure the gear system 92 to provide this operation. Particularly, the surgeon can hold the button 100 so that both of the shafts 86 and 88 rotate, and can selectively press the second button 102 when the surgeon wants the head portion 82 to stop rotating, but the outer shaft 86 to continue to rotate. The pistol grip 98 includes an internal chamber in fluid communication with the chamber 34 and a suction port 104 so that the cut-away material can be sucked out of the device 80, as discussed above.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A surgical device comprising:
    a body portion including a body chamber;
    a motor positioned in the body chamber;
    an elongated neck portion including a neck chamber;
    a first shaft coupled to the motor and extending through the neck chamber in the elongated neck portion, said first shaft including a shaft auger, said motor rotating the shaft;
    an open head portion coupled to the elongated neck portion, said first shaft extending into the open head portion, said open head portion including a plurality of cutting blades, where each cutting blade is an elongated member that extends the length of the head portion and is separated from adjacent cutting blades so as to define spaces therebetween to expose the auger and define the open part of the head portion;
    a second shaft coupled to the motor, said first shaft including an internal bore and said second shaft being positioned within the bore in a concentric manner with the first shaft, said head portion being rotatably coupled to the neck portion and rigidly coupled to the second shaft so that when the second shaft rotates the head portion rotates; and
    a suction port including a suction chamber in fluid communication with the neck chamber in the elongated neck portion, wherein the plurality of cutting blades are used to cut away material that falls into the open head portion, and wherein the cut away material is removed from the head portion into the neck chamber by the shaft auger and is removed from the neck chamber through the suction port.

2. The device according to claim 1 wherein each blade in the plurality of cutting blades is an arced cutting blade.

3. The device according to claim 1 wherein the plurality of cutting blades is four symmetrically disposed cutting blades.

4. The device according to claim 1 wherein each blade in the plurality of cutting blades includes a serrated cutting edge.

5. The device according to claim 1 wherein the elongated neck portion includes a wider diameter portion and a narrow diameter portion, wherein the wider diameter portion is opposite to the head portion.

6. The device according to claim 1 wherein the head portion is rotatably mounted to the elongated neck portion.

7. The device according to claim 6 wherein the head portion and the first shaft rotate in opposite directions.

8. The device according to claim 1 further comprising a first switch and a second switch, wherein the first switch is pressed to cause the first and second shafts to rotate and the second switch is pressed to stop the second shaft from rotating while the first switch is still being pressed.

9. The device according to claim 1 further comprising a seal positioned around the shaft between the neck chamber and the body chamber so as to prevent cut away material from entering the body chamber.

10. The device according to claim 1 further comprising a pistol grip, said suction port extending through the pistol grip.

11. The device according to claim 1 wherein the plurality of cutting blades is stainless steel.

12. The device according to claim 1 wherein the neck portion has a diameter of about 8 mm.

13. The device according to claim 1 wherein the neck portion has a length of about 9 inches.

14. The device according to claim 1 further comprising an irrigation channel for providing a liquid to the head portion.

15. The device according to claim 1 further comprising a shredding member positioned between the neck portion and the head portion, said shredding member shredding material that is drawn up the neck portion by the auger from the head portion.

16. The device according to claim 1 wherein the device is a spinal surgery device that is used to remove disc material between vertebrae during spinal fusion surgery.

17. A surgical device for removing disc material during a spinal fusion procedure, said device comprising:
    a body portion;
    a motor;
    an elongated neck portion including a neck chamber;
    a first shaft mounted to the motor and extending through the neck chamber in the elongated neck portion, said first shaft including a shaft auger, said motor rotating the shaft;
    an open head portion coupled to the elongated neck portion, said first shaft extending into the open head portion, said open head portion including a plurality of arced cutting blades each including a serrated cutting edge, said open head portion being rotatably mounted to the neck portion;
    a second shaft coupled to the motor, said first shaft including an internal bore and said second shaft being positioned within the bore in a concentric manner with the first shaft, said head portion being rotatably coupled to the neck portion and rigidly coupled to the second shaft so that when the second shaft rotates the head portion rotates; and
    a suction port coupled to the elongated neck portion, said suction port including a suction chamber in fluid communication with the neck chamber in the elongated neck portion, wherein the plurality of cutting blades cut away the disc material as the head portion rotates that falls into the open head portion, wherein the cut away disc material is removed from the head portion into the neck chamber by the shaft auger and is removed from the neck chamber through the suction port.

18. The device according to claim 17 wherein the elongated neck portion includes a wider diameter portion and a narrow diameter portion, wherein the wider diameter portion is opposite to the head portion.

19. The device according to claim 17 further comprising a first switch and a second switch, wherein the first switch is pressed to cause the first and second shafts to rotate and the second switch is pressed to stop the second shaft from rotating while the first switch is still being pressed.

20. The device according to claim 17 wherein the auger and the head portion rotate in opposite directions.

* * * * *